United States Patent [19]

Deindoerfer

[11] Patent Number: 4,667,335

[45] Date of Patent: * May 19, 1987

[54] METHOD OF DETERMINING THE DIAGNOSTIC SIGNIFICANCE OF THE CONTENT OF A VOLUME OF BIOLOGICAL SAMPLE CONTAINING PARTICLES

[75] Inventor: Fred H. Deindoerfer, Northridge, Calif.

[73] Assignee: International Remote Imaging Systems, Inc., Chatsworth, Calif.

[*] Notice: The portion of the term of this patent subsequent to May 2, 2002 has been disclaimed.

[21] Appl. No.: 736,432

[22] Filed: May 20, 1985

Related U.S. Application Data

[63] Continuation-in-part of Ser. No. 505,908, Jun. 20, 1983, Pat. No. 4,519,087.

[51] Int. Cl.⁴ .............................................. G01N 33/48
[52] U.S. Cl. .......................................... 377/10; 382/6; 356/39
[58] Field of Search ................. 377/10; 382/6; 356/39

[56] References Cited

U.S. PATENT DOCUMENTS

| | | | |
|---|---|---|---|
| 3,214,574 | 10/1965 | Landsman et al. | 377/10 |
| 3,315,229 | 4/1967 | Smithline | 377/10 |
| 3,970,841 | 7/1976 | Green | 250/201 |
| 4,021,117 | 5/1977 | Gohde et al. | 356/39 |
| 4,061,914 | 12/1977 | Green | 250/201 |

Primary Examiner—John S. Heyman
Attorney, Agent, or Firm—Limbach, Limbach & Sutton

[57] ABSTRACT

The present invention relates to a method for examining the content of a volume of biological sample containing particles to determine the diagnostic significance of that volume of biological sample. A number of aliquots of the sample are distributed and are examined under low power field magnification. The total number of aliquots examined under low power field magnification if a first fraction of the volume of biological sample. The percentage of particles detected in the first fraction is counted. The percentage of particles detected is compared to a first known percentage. In the event the comparison yields the result that the sample contains diagnostically insignificant number of particles, than the method is terminated. Otherwise the method is continued. A second fraction of volume of the biological sample, comprising a plurality of aliquots, is examined under high power field magnification. The percentage of particles detected under high power magnification is totalled. This is then compared to a second known percentage. The diagnostic significance of the biological sample is determined by the comparison of the second percentage of particles to the percentage of particles counted in the second fractional volume.

3 Claims, 4 Drawing Figures

U.S. Patent  May 19, 1987  Sheet 1 of 2  4,667,335
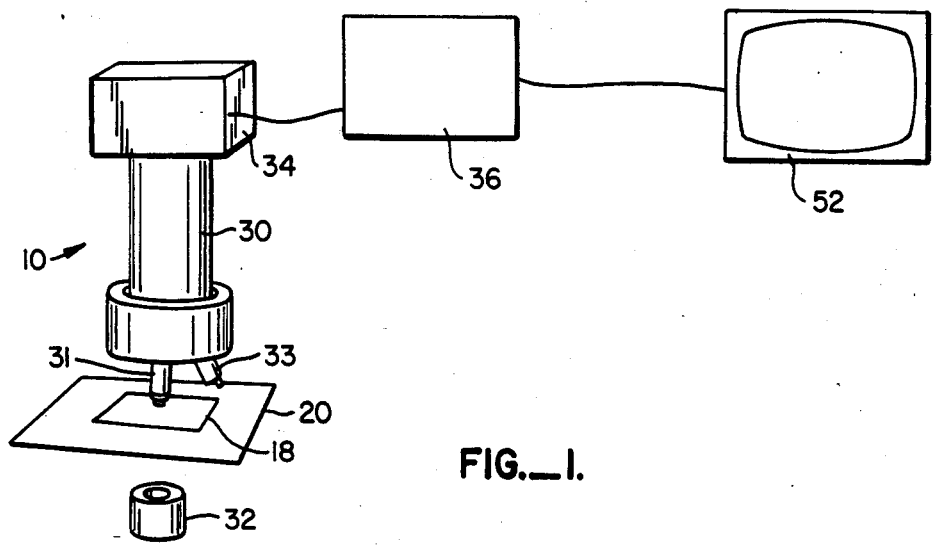
FIG._1.
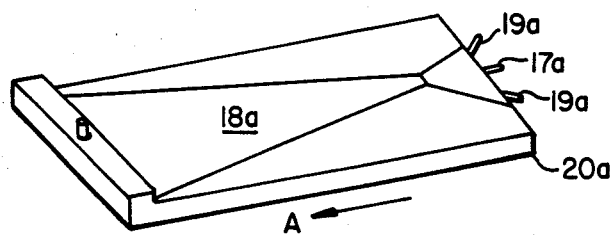
FIG._1a.
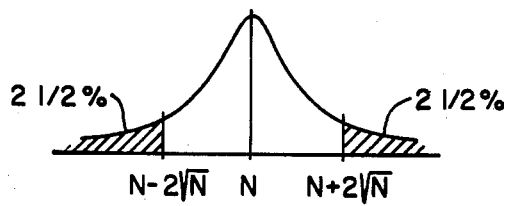
FIG._3.

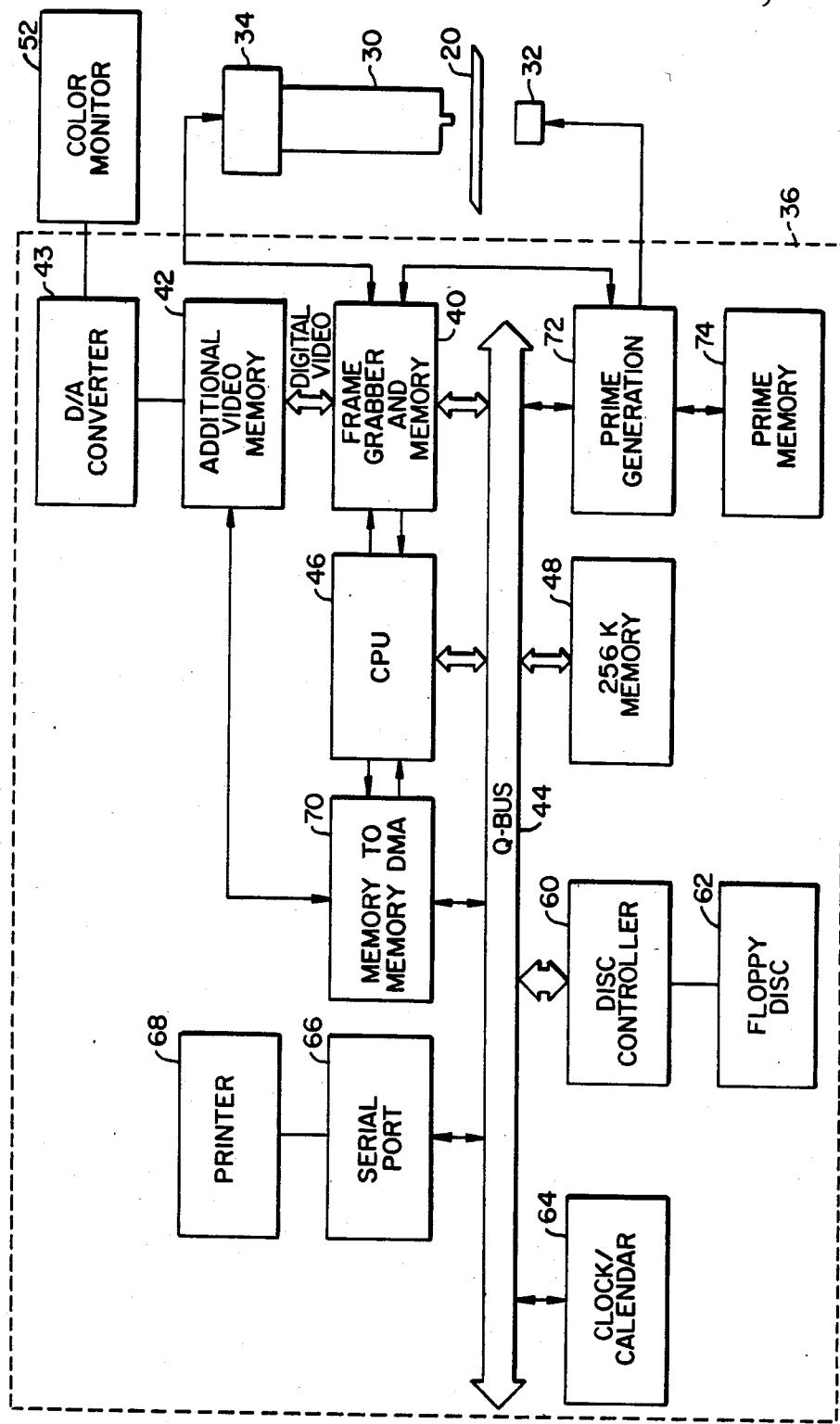
FIG._2.

METHOD OF DETERMINING THE DIAGNOSTIC SIGNIFICANCE OF THE CONTENT OF A VOLUME OF BIOLOGICAL SAMPLE CONTAINING PARTICLES

DESCRIPTION

This is a continuation-in-part application of a copending application entitled A Method Of Determining The Diagnostic Significance Of The Content Of A Volume Of Biological Sample Containing Particles, Ser. No. 505,908, filed June 20, 1983 and assigned to International Remote Imaging Systems, Inc. now U.S. Pat. No. 4,519,087.

1. Technical Field

The present invention relates to a method of determining the diagnostic significance of the content of a volume of biological sample containing particles, and, more particularly, to a two-stage method wherein a first fractional volume of said biological sample is analyzed under low-power magnification by a first microscopic means and then, if warranted, a second fractional volume of the sample is examined under high-power magnification by a second microscopic means.

2. Background Art

Heretofore, the method for examining the diagnostic significance of the content of a volume of biological sample containing particles is accomplished by placing an aliquot of the volume of biological sample under a microscopic means. The aliquot is examined for the presence of particles. These steps are repeated until a sufficiently large number of aliquots have been examined totalling a fractional volume of said sample. The number of particles detected within each aliquot examined is then totalled. The total number of particles is compared to the fractional volume. This number, such as X particles per unit volume of aliquot examined is compared to the threshold for determining the diagnostic significance for that unit volume of biological sample containing those particles. For example, with urine, if more than 3 red blood cells or more than 5 white blood cells are detected in a 400× field of view, then the sample of urine is generally considered diagnostically significant (sometimes units of volume are expressed as fields of view under a microscope).

All of this is predicated on the assumption that the number of aliquots examined is sufficient to represent a statistically sound sampling of the total volume of the biological sample. To ensure the statistical soundness of the examination, a large number of aliquots is examined. However, the examination of a large number of aliquots is extremely time-consuming. Moreover, the methods heretofore for determining the diagnostic significance of the content of a volume of biological sample containing particles have largely been done manually. Thus, error such as detection failure or misclassification of particles can occur as a result of eye strain and fatigue.

Method and apparatus for dual resolution of analysis of a cell has been accomplished. See, for example, U.S. Pat. Nos. 3,970,841 and 4,061,914. In both of these patents, however, a low resolution is used until an object of interest is detected. Thereafter, the object of interest is analyzed at a higher resolution while low resolution is continually used to analyze the scene. Neither patent teaches nor discloses a method for determining the diagnostic sionificance of the content of a volume of biological samples.

SUMMARY OF THE INVENTION

A method of determining the diagnostic significance of the content of a volume of biological sample containing particles is accomplished by examining a plurality of aliquots of the sample under low resolution. An optical still image of each aliquot is made. Each of the optical still images is converted to an electronic image. An electronic processor counts the number of particles in the electronic image. The aliquots are examined under low resolution until the number equals to a first a priori determined number of aliquots. The electronic processor totals the number of particles in the aliquots which have been examined under low resolution. The number of particles totalled is then compared to a first a priori determined number of particles. The method is terminated, based upon this comparison if the content of the volume of biological sample is deemed diagnostically insignificant. Otherwise, the method is continued. Another portion of the volume of biological fluid is examined. A second set of plurality of aliquots of the sample are examined under high resolution by a second microscopic means. An optical still image of each of the aliquots is formed. Each of the optical images is converted into an electronic image. The electronic processor determines the number of particles in each electronic image. The number of aliquots examined under high resolution is equal to a second a priori determined number of aliquots. The total number of particles within the aliquots examined under high resolution is then determined. The number of particles totalled in the second plurality of aliquots is then compared to a second a priori determined number of particles. The diagnostic significance of the content of the volume of biological sample is then determined based upon the comparison.

BRIEF DESCRIPTION OF THE DRAWINGS

FIG. 1 is a perspective view of an apparatus which can be used with the method of this invention.

FIG. 1a is a perspective view of a flow cell which can be used in the apparatus of FIG. 1.

FIG. 2 is a schematic diagram of the electronic processor employed by the apparatus of FIG. 1.

FIG. 3 is a graph of a statistical distribution and the probability of the count.

DETAILED DESCRIPTION OF THE INVENTION

The method of the present invention comprises distributing an aliquot of a volume of a biological sample containing particles over an extended area. The aliquot is examined under low resolution by a first microscopic means. The microscopic means forms an optical still image of the extended area. The optical image is converted into an electronic image. An electronic processor electronically counts the number of particles in the electronic image. These steps are repeated until the number of aliquots examined under low resolution equals to a first a priori determined number of aliquots. The total number of particles counted in the electronic images which represent the aliquots examined under low resolution is determined. The number of particles totalled is then compared to a first a priori determined number of particles. The method can be terminated based upon this comparison and the content of the volume of biological sample is deemed diagnostically insignificant.

Otherwise, the method is continued. An aliquot of a second fractional volume of biological sample is distributed over an extended area. The aliquot is examined under high resolution by a second microscopic means. An optical still image of the extended area is formed. The optical image is converted into an electronic image. An electronic processor counts the number of particles in the electronic image. These steps are repeated until the number of aliquots examined under high resolution equals to a second a priori determined number of aliquots. The total number of particles in the total aliquots examined under high resolution is counted. The number of particles totalled is then compared to a second a priori determined number of particles. The diagnostic significance of the biological sample is then determined based upon this comparison.

The method of the present invention may be practiced by using an apparatus 10, shown in FIG. 1. The apparatus 10 includes a microscope 30, which has a low power resolution lens 31 and a high power resolution lens 33. Each of the lenses, 31 or 33, can be focused on an examination area 18 of the microscope slide 20. Each aliquot of the biological sample is distributed over the microscopic slide 20. The examination area 18 is illuminated below by a strobe light 32 which is preferably a U.S. Scientific Instrument Corporation Model 3018, containing a 2UP1.5 lamp. The light 32 is directed at the microscope 30 in a direction substantially parallel to the thickness of the slide 20. The strobe light 32 operates, preferably, at 1/60th of a second, thereby forming a series of still optical images at the microscope 30.

The output of the microscope 30 is focused on a camera 34 which is preferably a Vidicon camera model number KY1900'manufactured by JVC Corporation. The camera 34 converts each optical image into an electronic image. The analog-to-digital converter associated with the camera 34 also segments each of the electronic images into a plurality of pixels, with each pixel corresponding to a defined portion of each image. The plurality of electronic images (each optical image is converted into an electronic image) contains images of the particles. Since the biological sample may be dilute, such as urine, it is possible that not every electronic image contains an image of a particle or particles.

The electronic images are then passed from the camera 34 to the processor 36. The processor 36 extracts from the electronic image the images of the particles. The images of the particles can be displayed on display 52 in an order arrayed by classes of visually discernible characteristics.

The method of the present invention can also be practiced by the use of flow cell 20a shown in FIG. 1a. The flow cell 20a is of the type fully described in U.S. Pat. No. 4,338,024. A sample fluid, such as urine, is sent into the flow cell 20a through first input 17a. Sheath fluids are provided to the flow cell 20a through the second input 19a. The sample fluid is moved through the flow cell 20a in the direction shown by arrow A. The sample fluid is distributed over an extended area 18a, which has a width many times the thickness, with each measured perpendicular to the direction of flow. The sample fluid is distributed with essentially no particle overlapping other particles in the extended area 18a. The sample fluid in the flow cell 20a is placed under the microscope 30 such that the microscope 30 focuses on the extended area 18a. As the sample fluid moves through the flow cell 20a, the microscope 30 takes an optical image of the fluid in the viewing area 18a. Since the fluid is moving, the apparatus 10 is held stationary. Thus, the images formed at the microscope 30 are of different portions of the sample fluid.

The processor 36 is shown in greater detail in block schematic form in FIG. 2.

The processor 36 includes a frame grabber and memory 40 which receives the electronic image from the camera 34. The frame grabber 40 can be a module which is available from Matrox Corporation of Montreal. Preferably, the frame grabber 40 is a Model 101-0009 CRT/IO Module from International Remote Imaging Systems, Inc. of Chatsworth, Calif. The output of the frame grabber and memory 40 is supplied to an Additional Refresh Video Memory 42, which comprises a 64K dual ported luminance memory and a 32K dual ported R-Y and B-Y memory. The output of the Refresh Video Memory 42 is connected to a D/A converter 43 which is coupled to the color monitor 52.

The Frame Grabber and Memory 40 is also coupled to a Q-Bus 44 of the Central Processing Unit 46, which is preferably a Telesoft T68 Central Processing Unit. 256K of memory 48 from Chrislin Industries Inc. is also connected to the Q-Bus 44. In addition, a disc controller 60, with a floppy disc drive 62 attached thereto, is also connected to the Q-Bus 44. The processor 36 also comprises a clock/calendar 64 connected to the Q-Bus 44. A serial port 66 with a printer 68 are also connected to the Q-Bus 44. A Memory-to-Memory DMA 70 controls transfer of images from the frame grabber 40 to the additional Video Memory 42. The grame grabber 40 also activates the srobe 32. Finally, a prime generator 72 with a prime memory 74 are also connected to the Q-Bus 44.

Each electronic image from the camera 34 is stored in the Frame Grabber and Memory 40. The CPU 46 operates on the electronic image received by the processor 36. The processed images are stored in the Memory 42 which are supplied to the Monitor 52 for display. For long term storage, the images can be stored on the floppy disc 62. The prime generator 72 detects the edge of the particle in the electronic image. The operation of the prime generator 72 is the subject of a pending U.S. application, Ser. No. 470,208, filed Feb. 28, 1983, and is incorporated herein by reference.

In the method of the present invention, an aliquot of the volume of biological sample which contains particles is distributed over an extended area. The aliquot may be distributed over microscopic slide 20 or it may be passed through the flow cell 20a of FIG. 1a. Each aliquot is examined under low resolution by microscope 30 with low resolution lens 31. The microscope 30 forms an optical still image of the extended area 18 of the microscopic slide 20 or of 18a of the flow cell 20a. Each optical image is converted into an electronic image by the camera 34. The processor 36 electronically counts the number of particles in each of the electronic images from the camera 34.

These steps are repeated until the number of aliquots examined under low power resolution equals a first a priori determined number of aliquots. The first a priori determined number of aliquots represents a first fraction of the volume of biological sample. The number of particles detected in this first fraction of volume of biological sample (or the total number of aliquots examined under low power resolution) is counted. This number of particles detected in the first fraction volume of biological sample is then compared to a first a priori determined number of particles. Based upon this comparison, the method of the present invention is either terminated in which case the content of the volume of biological sample is diagnostically insignificant or the method is continued.

In the event the method is continued, an aliquot of the volume of biological sample is distributed over the extended area 18 or 18a. The aliquot is again examined, but this time under high power resolution by microscope 30 with high power resolution lens 33. An optical still image of the extended area is formed. The optical image is then converted to an electronic image by camera 34. The processor 36 electronically counts the number of particles in the electronic images.

The steps of distributing the aliquot, forming the optical still image, converting each optical image to an electronic image, and electronically counting the number of particles in each electronic image is repeated until the number of aliquots examined under high power resolution equal to a second a priori determined number of aliquots. The second a priori determined number of aliquots being equal to a second fractional volume of biological sample. The total number of particles in this second fractional volume of biological sample is then counted. The total number of particles counted in the second fractional volume of biological sample is compared to a second a priori determined number of particles. The diagnostic significance of the biological sample is then determined based upon this comparison.

As can be seen from FIG. 1, the low power resolution lens 31 and the high power resolution lens 33 can all be the same part of the same microscope 30.

The theory of the present invention can be understood as follows. The biological sample under analysis has a threshold for determining its diagnostic significance. For example, with urine, if more than three red blood cells or more than five white blood cells are detected in a HPF (or 400× field of view of its sediment) sample of urine is generally considered diagnostically significant. As previously stated, units of volume can be expressed as fields of view under the microscope. In general, therefore, with any biological sample, there is a threshold level for the diagnostic significance of that kind of biological sample. That number, can be expressed as X particles/unit volume of the bio-logical sample. The threshold level can be greater than X particle/unit volume (as in the case of urine, i.e., greater than 3 RBC or 5 WBC/HPF, or it can be less than X particle/unit volume (as in the case of blood, for example, if less than X RBC/unit volume is detected, the sample of blood is deemed to be diagnositally significant as indicating possible anemia.) Therefore, with any biological sample, there is a threshold number indicative of the diagnostic significance of that type of biological sample, generally designated as X particles/unit volume.

When a volume of the particular biological sample is analyzed under the method of the present invention, a first fractional volume of the biological sample is chosen. The first fractional volume is examined under low power resolution. The first fractional volume is comprised of a plurality of units of volume or aliquots. Within that first plurality of units of volume of volume, the particular particules of interest are totalled. Thus, for example, if a urine sample is presented for analysis, a first fractional volume comprising of Y HPF's is analyzed and Z number of RBC particles are detectd, then these numbers are compared to the threshold number.

The problem, however, with counting is the precision of the count. In general, the precision varies as $1/N$, where N is the number counted. More particularly, if N particles are counted, then there is a ninety-five percent (95%) probability that the actual count lies in the range $N \pm 2\sqrt{N}$. Thus, if Z particles are detected in the examination of Y units of volume, the range of concentration of those Z particles per unit of volume (with approximately 95% probability) can be expressed as $(Z \pm 2\sqrt{Z})$. Comparing this to the threshold value of X particles per unit of volume, one then gets a determination of the diagnostic significance of the sample being examined.

The theory can best be shown by the following examples.

EXAMPLE 1

The biological sample is urine and for urine; the threshold diagnostic significance is greater than or equal to 3 RBC or 5WBC particles/HPF. In a sample of urine, a first fractional volume of the sample is analyzed under low resolution.

The volume viewed under low resolution is sixteen (16) times the volume viewed under high resolution. The threshold diagnostic significane under low power resolution then becomes greater than or equal to 48 RBC particles/LPF or 80 WBC particles/LPF. Since RBC and WBC type particle cannot be accurately differentiated under low power resolution, the lower threshold of 48 RBC or WBC type particle/LPF is used.

It is desired that the number of frames in this first fractional volume to be examined be the volume equivalent of one (1) LPF. The sample of urine is examined for this number of frames. The number of blood cell size particles in this volume is totalled.

Suppose, the number of particles found is 25 such particles. There is a ninety-five percent (95%) probability that the number of particles detected lies in the range $25 \pm \sqrt{25}$ or between 15 and 35. Since the specimen contains less than 48 RBC type particle/LPF or 3RBC type particle/HPF, the method is terminated and the sample is deemed diagnostically insignificant.

EXAMPLE 2

Similar to example 1, urine is the biological sample. Again, the focus will be on RBC type particle and the diagnostic significance for urine under the low power resolution is greater than or equal to 48 such particles/LPF. The first fractional volume is one LPF.

Suppose the number of RBC type particle detected under low power is 49. There is a ninety-five percent (95%) probability that the number of particles detected lies in the range $49 \pm 2\sqrt{49}$ or between 35 and 63. Since it is possible that 63 RBC type particles are detected in one LPF, and since this number exceeds 48 particles/LPF, further analysis under high power resolution is needed.

Suppose under high power resolution it is found that for each HPF volume, the following particles are found:
1 Calcium Oxalate particle
1 RBC
1 WBC Since this is less than 3 RBC/HPF or 5 WBC/HPF, the specimen is diagnostically insignificant.

EXAMPLE 3

Again, urine is examined and RBC type particles are analyzed. In this example, again, one LPF is examined, and with the diagnostic threshhold being 48 RBC type particle/LPF.

Suppose 8 RBC type particles are detected. The probability distribution is that there is ninety-five percent (95%) probability of the count lying in the range between 63 and 99 particles. The examination then proceeds to high resolution.

Under high resolution four (4) RBC/HPF and one (1) WBC/HPC are detected. This is diagnostically significant and is indicative of microhematuria.

EXAMPLE 4

In this example urine is examined. The same facts in the other examples apply.

Under low resolution 2500 RBC type particles are detected. The range of probability of this count is between 2400 and 2600. The entire range exceeds 48.

Under high resolution, it is determined that 140 WBC/HPF and 10 RBC/HPF are present. This is diagnostically significant and indicates pyuria and hematuria.

By examining the biological sample under low power resolution first, a greater amount of the sample can be initially examined. An examination of an aliquot under high power field magnification means each high power field can examine a smaller volume of the sample than low power field examination of an aliquot. Thus, by dividing the method of the present invention to first examining the biological sample under low power field magnification and then, if need be, switch to high power field magnification, means that the number of specimen which can be examined is increased.

From the foregoing, it can be seen that instead of counting to a certain precision; i.e., a predetermined number, the invention is also applicable to counting to a certain precision where the a priori threshold is expressed as a percentage. In that event, once in the low resolution mode, if the threshold of the percentage of particles has been exceeded, then the invention proceeds to count the significance of particles in the high resolution mode. Thus, in the first example, if the percentage of RBC or WBC type particle under LPE is x% and y% of such particles is detected, then if x>y then the method is terminated. Conversely, if x≦y then the sample is examined under HPF.

I claim:

1. A method of determining the diagnostic significance of the content of a volume of biological sample containing particles, said method comprising the steps of:
    (a) distributing an aliquot of said sample over an extended area;
    (b) examining the aliquot under low resolution by a first microscopic means;
    (c) forming an optical still image of said extended area;
    (d) converting said optical image to an electronic image;
    (e) electronically counting the percentage of said particles in said electronic image;
    (f) repeating the steps of (a)–(e) until the number of aliquots examined under low resolution equals a first a priori determined number of aliquots;
    (g) totalling the percentage of particles in said aliquots examined under low resolution;
    (h) comparing said percentage of particles to a first a priori determined percentage of particles;
    (i) terminating said method, based upon said comparison, the content of said volume of biological sample being diagnostically insignificant; otherwise
    (j) continuing said method based upon said comparison;
    (k) distributing an aliquot of said sample over an extended area;
    (l) examining the aliquot under high resolution by a second microscopic means;
    (m) forming an optical still image of said extended area;
    (n) converting said optical image to an electronic image;
    (o) electronically counting the percentage of particles in said electronic image;
    (p) repeating the steps of (k)–(o) until the number of aliquots examined under high resolution equals a second a priori determined number of aliquots;
    (q) totalling the percentage of particles in said aliquots examined under high resolution;
    (r) comparing said percentage of particles to a second a priori determined percentage of particles;
    (s) determining the diagnostic significance of the content of said biological sample based upon said comparison.

2. The method of claim 1 wherein said first microscopic means and said second microscopic means are the same microscopic means.

3. The method of claim 1 wherein said biological sample is urine.

* * * * *

UNITED STATES PATENT OFFICE
CERTIFICATE OF CORRECTION

Patent No. 4,667,335    Dated May 19, 1987

Inventor(s) Fred H. Deindoerfer

It is certified that error appears in the above-identified patent and that said Letters Patent are hereby corrected as shown below:

In the Abstract,   Line 7    "if" should be -- is --

Signed and Sealed this

Ninth Day of February, 1988

Attest:

DONALD J. QUIGG

*Attesting Officer*    *Commissioner of Patents and Trademarks*